US008577461B2

(12) United States Patent
Vaska

(10) Patent No.: US 8,577,461 B2
(45) Date of Patent: Nov. 5, 2013

(54) DEVICES AND METHODS FOR ABSORBING, TRANSFERRING AND DELIVERING HEART ENERGY

(76) Inventor: Matthias Vaska, Palo Alto, CA (US)

( * ) Notice: Subject to any disclaimer, the term of this patent is extended or adjusted under 35 U.S.C. 154(b) by 433 days.

(21) Appl. No.: 12/909,630

(22) Filed: Oct. 21, 2010

(65) Prior Publication Data

US 2011/0034754 A1 Feb. 10, 2011

Related U.S. Application Data

(63) Continuation of application No. 12/005,684, filed on Dec. 27, 2007, now Pat. No. 7,841,977, which is a continuation-in-part of application No. 11/474,054, filed on Jun. 22, 2006, now abandoned.

(51) Int. Cl.
*A61N 1/362* (2006.01)

(52) U.S. Cl.
USPC ............... 607/35; 607/34; 607/142; 607/148; 607/149; 600/16

(58) Field of Classification Search
USPC ................. 607/34, 35, 142, 148, 149; 600/16
See application file for complete search history.

(56) References Cited

U.S. PATENT DOCUMENTS

| 4,888,011 | A | * | 12/1989 | Kung et al. .................. 623/3.24 |
| 4,957,477 | A | | 9/1990 | Lundback |
| 6,432,039 | B1 | | 8/2002 | Wardle |
| 7,468,029 | B1 | | 12/2008 | Robertson et al. |
| 7,841,977 | B2 | | 11/2010 | Vaska |

* cited by examiner

*Primary Examiner* — Christopher D Koharski
*Assistant Examiner* — Natasha Patel
(74) *Attorney, Agent, or Firm* — Jens E. Hoekendijk

(57) ABSTRACT

A device for altering cardiac performance includes an energy absorbing element which absorbs cardiac pumping energy from at least a portion of the heart. The energy may be delivered to another part of the body, such as another portion of the heart, to perform useful work such as providing blood pumping assistance.

15 Claims, 14 Drawing Sheets

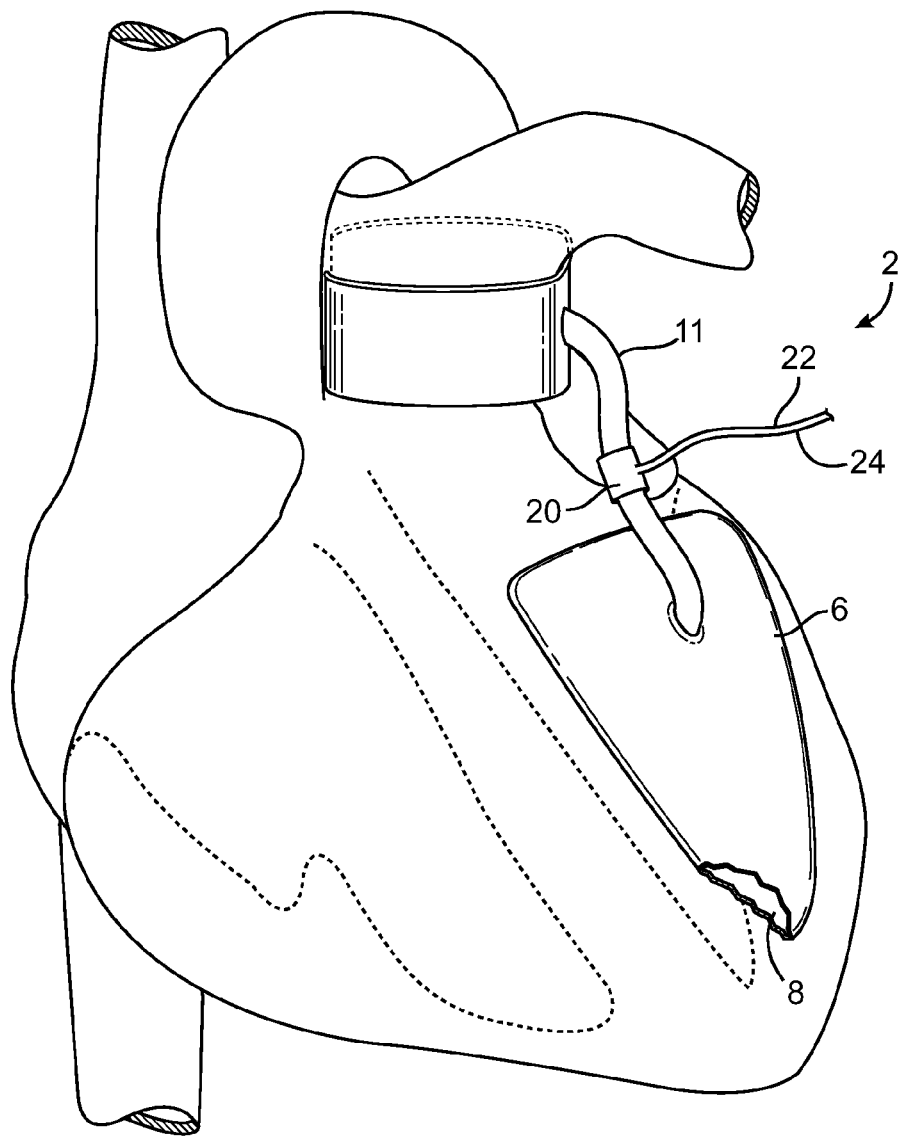
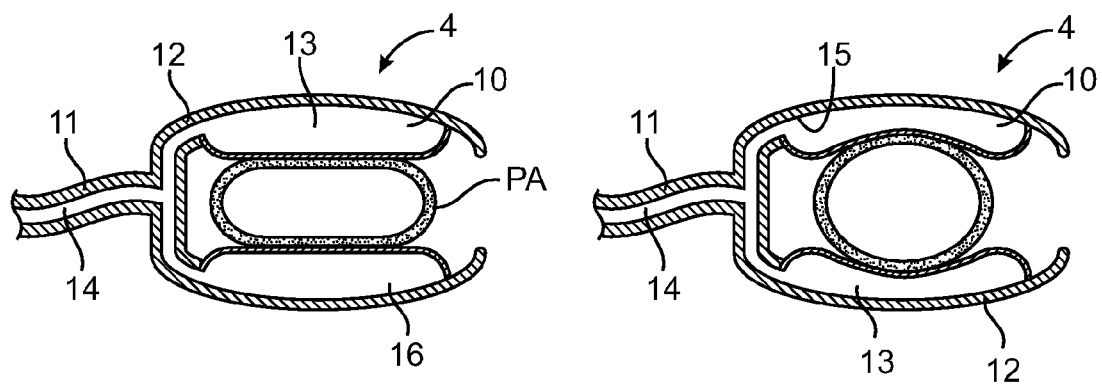
FIG. 1
FIG. 2
FIG. 3

DEVICES AND METHODS FOR ABSORBING, TRANSFERRING AND DELIVERING HEART ENERGY

This application is a continuation of application Ser. No. 12/005,684, filed on Dec. 27, 2007 now U.S. Pat. No. 7,841,977 (now allowed), which is a continuation-in-part of application Ser. No. 11/474,054, filed on Jun. 22, 2006 now abandoned. The full disclosures of which are hereby incorporated by reference.

BACKGROUND

Heart failure is a serious disease that is caused by deterioration of ventricular muscle. This deterioration ultimately reduces the ability of the heart to pump blood, causes a number of severe symptoms, and results in a high mortality rate.

Many heart failure patients have left ventricular dysfunction wherein the left ventricle is diseased while the right ventricle remains relatively healthy. Because the right and left ventricle are fluidly connected in series, both ventricles must pump the same amount of blood. Therefore with left ventricular dysfunction, the healthier right ventricle is forced to reduce its output to that of the left ventricle. The mechanism by which this occurs is a significant increase in blood pressures against which the right heart must work. Over time, this additional stress on the right ventricle can cause right ventricular dysfunction.

Various electric and pneumatic pumps have been proposed that assist failing hearts in pumping blood. Left ventricular assist devices, for example, remove blood from the left ventricle and pump into the aorta, thereby unloading the diseased left ventricle and improving cardiac output. Because the right heart is often healthy, often no assist is provided to the right ventricle. Since assist devices must put energy into pumping blood, an energy source is required. This energy source is usually electric. Reliably providing the amount of energy needed to assist the heart significantly increases the complexity of these assist devices. Power systems often include an electric pump, an internal battery, external batteries, chargers, control systems, and a skin port (for an electrical wire or vent) or transcutaneous energy transmission (TET) coils. These various components increase cost and can result in reliability and ease-of-use problems. In addition, the implantation of these components can be time consuming and difficult. Furthermore, the blood-contacting nature of many assist devices results in significant complications (e.g., stroke).

Cardiomyoplasty was an experimental procedure that attempted to achieve active heart assist without external power. The idea was to harvest muscle from other parts of the body, wrap it around the heart, and electrically activate it in synchrony with the heart. The concept has met with little success.

SUMMARY OF THE INVENTION

The present invention involves absorbing cardiac energy used to pump blood and delivering this energy to another portion of the vascular system in a way that assists the overall function of the heart. For example, the present invention can be used to treat heart failure patients with left ventricular dysfunction who have a relatively healthy right ventricle. The invention may provide active assist to the left ventricle by taking advantage of the unused extra capacity of the healthier right ventricle. The device and method thereby avoid the need for external power while still actively assisting the left ventricle. Of course, the invention may also be used with an active assist which adds pumping energy to the system as well. The invention also benefits from a simple and compact design which facilitates implantation and reliability. Furthermore, some embodiments may be designed to avoid blood contact entirely and be placed on a beating heart using minimally invasive access, thereby minimizing potential complications.

An energy absorbing portion of the system may be implanted in or on the right side of the heart that is designed to convert right ventricular energy into a form that can be transferred by an energy delivery portion to the left ventricle. For example a device could be configured to change the pressure of a fluid when the right ventricle contracts. This fluid could then be delivered through a lumen to the left ventricle where the change in pressure and/or volume is used to help the left ventricle pump. Because the left and right ventricles contract at the same time, there is no need to provide any synchronization function (i.e., the fluid is moved at the appropriate time). Of course, other devices and methods for absorbing energy from the right ventricle and transferring it to the left ventricle (or vice versa), such as those that incorporate cables and linkages, could be used without departing from the scope of the invention. The energy absorbing element could be formed as a clip configured to fit around the pulmonary artery (PA). This clip may have at least one expandable or compressible member positioned between the clip and the PA. The expandable member may be a bladder containing a fluid. When the heart is in diastole (i.e., ventricles are filling) the blood pressure in the PA is relatively low, and the bladder is configured to gently squeeze the PA in order to reduce its cross-sectional area and volume. This could be accomplished by constructing the bladder with a bias toward a pre-determined expanded shape that provides this squeezing effect when it is under a relatively small amount of stress.

When the right ventricle contracts the pressure in the PA rises, thereby squeezing the bladder between the PA and the clip which is substantially rigid. The bladder is configured to collapse under these conditions, increasing the pressure of the fluid inside the bladder and forcing the fluid out of a lumen connected to the bladder. The lumen conveys the fluid in a tube and the other end of this lumen is connected to an expandable element that is configured to be placed on the exterior surface of the left ventricular free wall. As the fluid enters the expandable element, pressure is applied to the left ventricular free wall thereby aiding left ventricular contraction. When ventricular contraction (i.e., systole) is complete the pressure in the PA falls, causing the bladder to expand. This pulls fluid out of the expandable element, allowing the left ventricle to fill properly.

Of course, other portions of the right heart system, such as the right ventricle or any portion of the pulmonary arterial tree which shall mean the pulmonary artery and its branches as used herein, could be used as a source of energy without departing from the scope of the invention. For example, a balloon-like device placed inside the right ventricle or pulmonary arterial tree would provide a similar functionality. Similarly, other portions of the left heart system, such as the aorta, could be used to help in pumping without departing from the scope of the invention. For example, the device could be configured to squeeze the aorta during diastole in order to achieve an effect similar to intra-aortic balloon pumps. These and other configurations within the scope of the invention are described below.

DESCRIPTION OF DRAWINGS

FIG. 1 shows a device for assisting the heart in pumping blood which has an energy absorbing element and an energy delivering element FIG. 2 is a cross-sectional view of the energy absorbing element.

FIG. 3 is a cross-sectional view of the energy absorbing element with a compressible element being compressed when the pulmonary artery expands.

DETAILED DESCRIPTION

Figure 4:
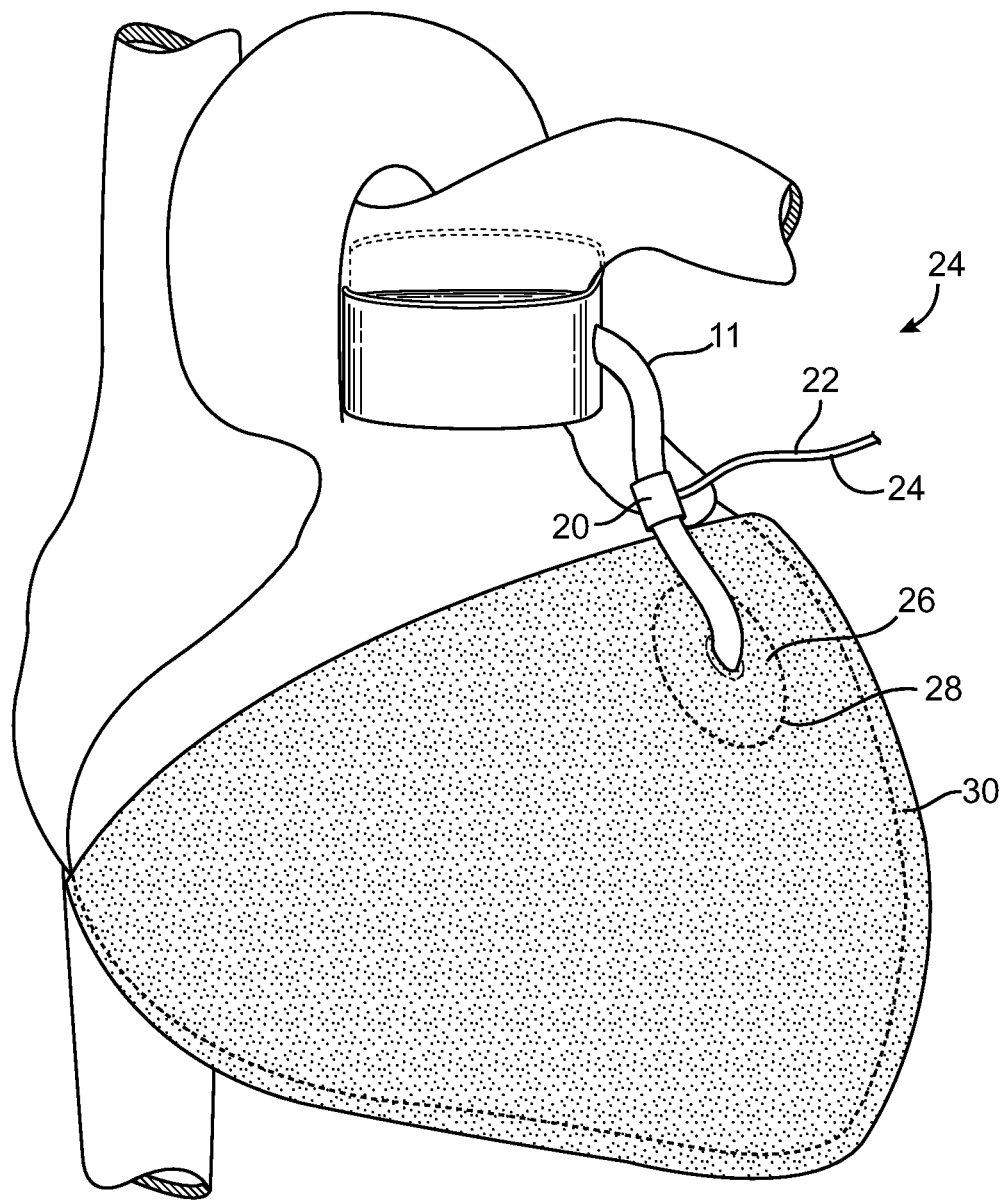
FIG. 4 shows another device for assisting the heart in pumping blood which has an element extending around the heart that reduces dilatation of the heart.

Referring to FIGS. 1-3, a device 2 for assisting the heart in pumping blood is shown. The device 2 has an energy absorbing element 4 which absorbs pumping energy of the heart. The device 2 also has an energy delivery element 6 which receives energy from the energy absorbing element 4 and uses the energy to provide pumping assistance to the heart. The energy delivery element 6 may include an expandable element 8 placed adjacent to an exterior surface of the left ventricle. The expandable element 8 applies pressure to the exterior surface of the left ventricle during contraction of the left ventricle to assist the left ventricle in pumping blood.

The energy absorbing element 4 is configured and positioned to absorb pumping energy from the heart when the right ventricle is contracting. The energy absorbing element 4 may be positioned around at least a portion of a blood vessel that is part of the pulmonary arterial tree such as one of the pulmonary arteries. The energy absorbing element 4 has a compressible element 10 which is compressed when pressure increases in the blood vessel. The energy absorbing element 4 may have a substantially rigid collar or clip 12 which extends around the blood vessel with the compressible element 10 positioned on a radially inner side 15 of the collar 12 between the collar 12 and the pulmonary artery PA.

The expandable element 8 of the energy delivery element 6 and the compressible element 10 of the energy absorbing element 4 may each contain a fluid 13. The fluid in the elements 8, 10 are in pressure communication with one another, either directly or indirectly, so that an increase in fluid pressure in the compressible element produces an increase in fluid pressure in the expandable element. The elements 8, 10 are coupled together via a tube 11 having a lumen 14 so that the same fluid 13 is transferred between the two elements 8, 10. The fluid 13 in the two elements 8, 10 may also be kept separate with a pressure communicating element, such as a flexible septum (not shown), which communicates fluid pressure between the two elements 8, 10 without mixing the fluids in the elements 8, 10.

The compressible element 10 may be any suitable structure such as a bladder 16. When the heart is in diastole (i.e., ventricles are filling) the blood pressure in the PA is relatively low, and the compressible element 10 is configured to gently squeeze the PA in order to reduce its cross-sectional area and volume. This could be accomplished by constructing the compressible element 10 with a bias toward a pre-determined expanded shape which is smaller than the relaxed shape of the PA as shown in FIG. 2 so that the compressible element 10 squeezes the PA when it is under a relatively small amount of stress. When the right ventricle contracts the pressure in the PA rises, thereby squeezing the bladder 16 between the PA and the collar 12 as shown in FIG. 3. The bladder 16 is configured to collapse under these conditions, increasing the pressure of the fluid inside the bladder 16 and forcing the fluid through the lumen 14 connected to the bladder 16.

The fluid in the lumen 14 is in pressure communication with fluid in the expandable element 8 positioned on the exterior surface of the left ventricular free wall. As the fluid enters the expandable element 8, pressure is applied to the left ventricular free wall thereby aiding left ventricular contraction. When ventricular contraction (i.e., systole) is complete the pressure in the PA falls, causing the bladder 16 to expand which pulls fluid out of the expandable element 8 thereby allowing the left ventricle to fill. A valve 20 may also be placed along the lumen 14 in order to adjust the amount of fluid that is allowed to pass through the lumen 14. Slowly opening the valve 20 with a remote operating device 22, such as a cable or tube 24, may be useful in allowing the right ventricle to adjust to its new pumping conditions. Such a valve 20 may be incorporated into any of the embodiments described herein and such configurations are explicitly incorporated.

The expandable and compressible elements 8, 10, such as the bladder 16, and the tube 11 may be constructed of any suitable materials. For example, the elements 8, 10 and tube 11 may be constructed of implant grade biocompatible elastomers such as polyurethane and silicone. The material, thickness, and shape of the expandable and compressible elements 8, 10 are selected such that significant motion of the expandable and compressible elements 8, 10 occurs when pressure differentials are applied inside and outside the elements. The pressure differentials are caused by the varying blood pressures and wall tensions of the portions of the vasculature that are in contact with the expandable and compressible elements 8, 10. The clip or collar 12 may be constructed of stainless steel or an implant grade biocompatible thermoplastic such as polyetheretherketone (PEEK). The fluid may be air, carbon dioxide, saline, or any other suitable gas or liquid.

Referring to FIG. 4, another device 24 for assisting the heart in pumping blood is shown which is similar to the device of FIGS. 1-3. An energy delivery element 26 has an expandable element 28 positioned against an exterior wall of the left ventricle. A constraining element 30 extends around the heart which may prevent undesirable distension of the heart. The constraining element 30 extends over the expandable element 28 and may be used to anchor the expandable element 28. Any of the devices described herein may be combined with the constraining element 26 which may be used to help hold portions of the device in place while also providing a compression force which may reduce undesirable distension of the heart.

Figure 5:
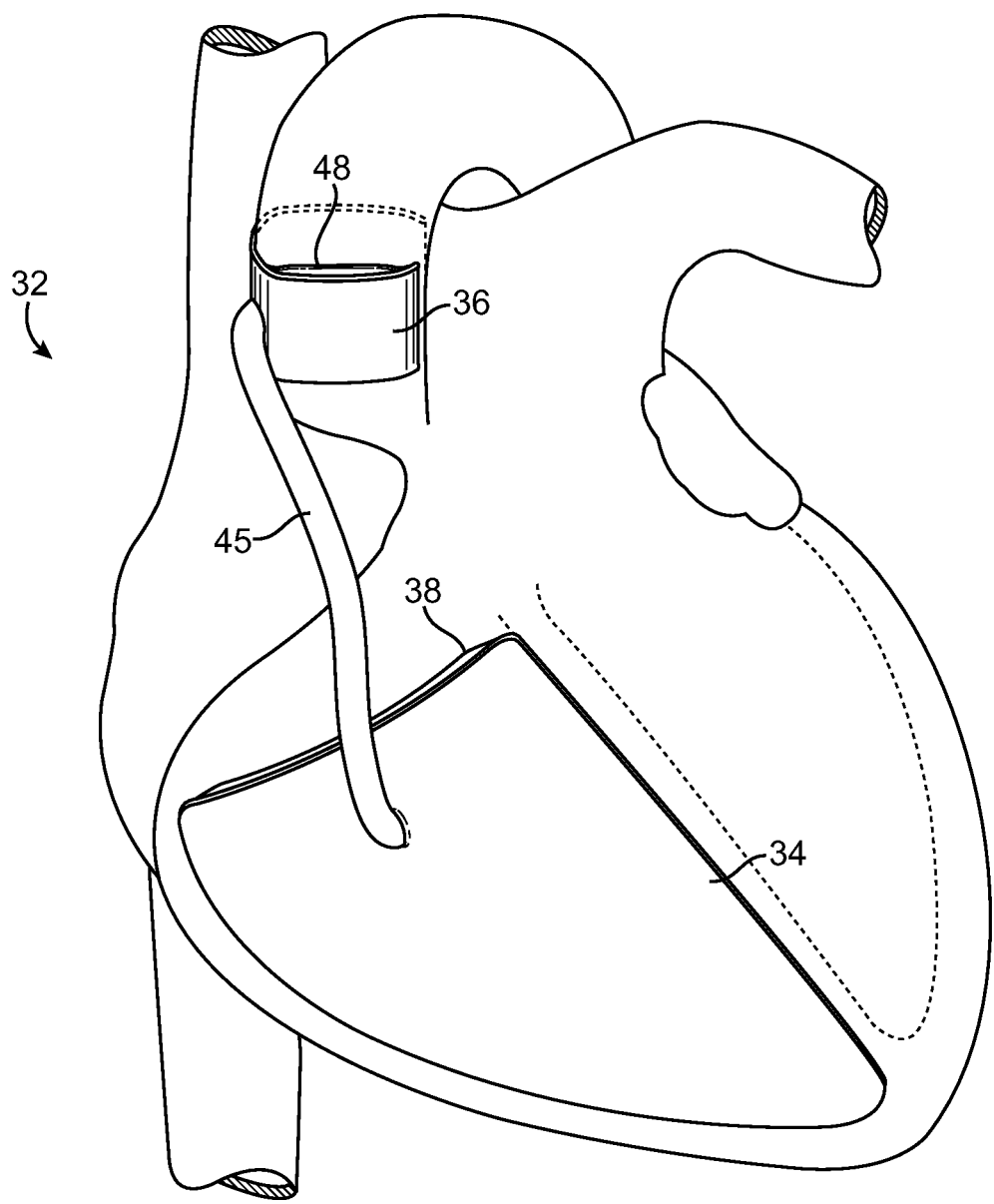
FIG. 5 shows another device for assisting the heart in pumping blood.
Figure 6:
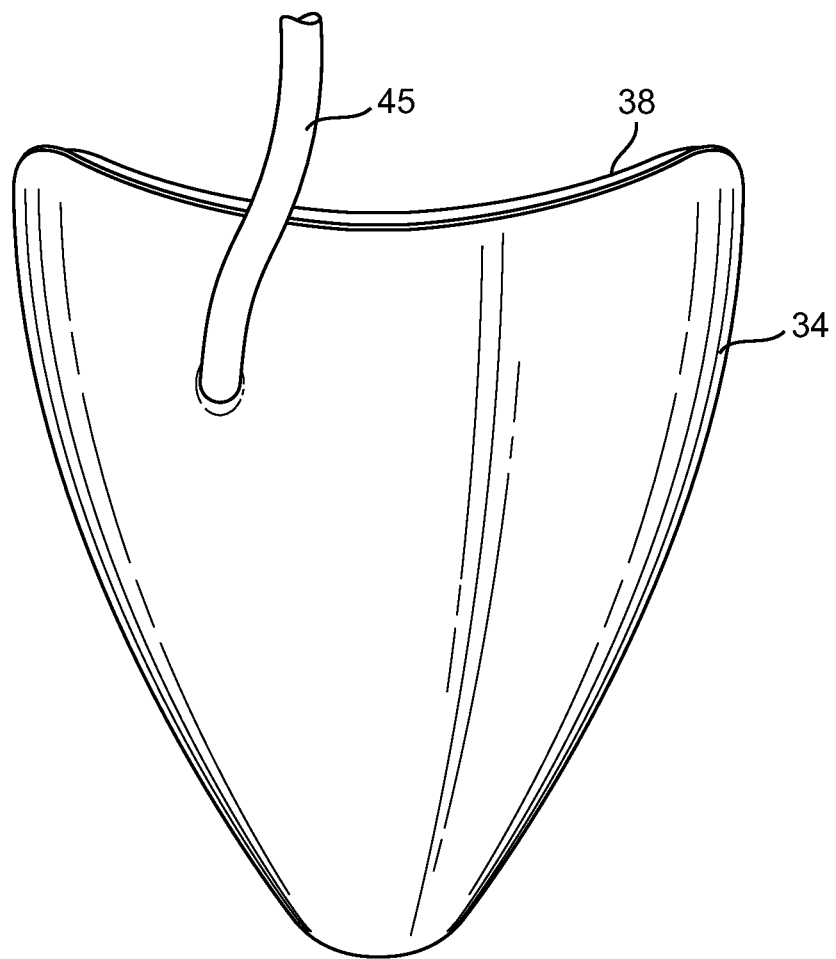
FIG. 6 shows the energy absorbing element of the device of FIG. 5.
Figure 7:
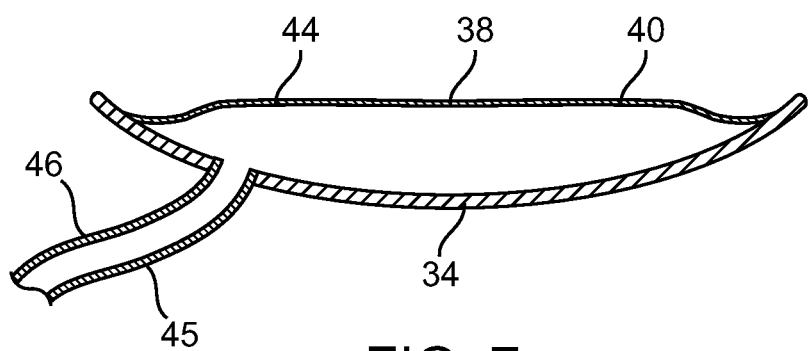
FIG. 7 shows a cross-sectional view of the energy absorbing element of FIG. 5.

Referring to FIGS. 5-7, another device 32 for absorbing and delivering cardiac energy is shown. The device 32 has an energy absorbing element 34 positioned adjacent an exterior surface of the right ventricle to move fluid to and from an energy delivery element 36 positioned on the aorta or a branch vessel of the aorta. The energy absorbing element 34 may have an expandable element 38 such as a bladder 40 which may have a substantially rigid convex outer surface 42 that is configured to contact the pericardium. Outer edges of the surface 42 may be configured to contact the heart near the interventricular septum and atrioventricular groove. A flexible interior surface 44 may be attached to the epicardial surface of the right ventricular free wall using a surgical adhesive such as cyanoacrylate or by promoting the formation of biological adhesions.

When the right ventricle contracts, the bladder 40 expands and the pressure of the fluid inside the bladder 40 is reduced. A tube 45 having a lumen 46 is attached to the bladder 40 to provide pressure communication with an expandable and collapsible element 48 on the energy delivery element 36. The energy delivery element 36 may take any suitable shape such as the clip 12 and element 10 of FIGS. 1-3. Thus, the aorta or branch vessel is squeezed by the expandable and collapsible element 48 of the energy delivery element 36 during diastole when the aortic pressure is lower. During systole, the energy absorbing element 34 pulls fluid out of the collapsible element 48 causing the element 48 to collapse thereby increasing the volume inside the aorta. This aortic volume increase during systole allows the left ventricle to pump more easily in a manner similar to intra-aortic balloon pumping.

Figure 8:
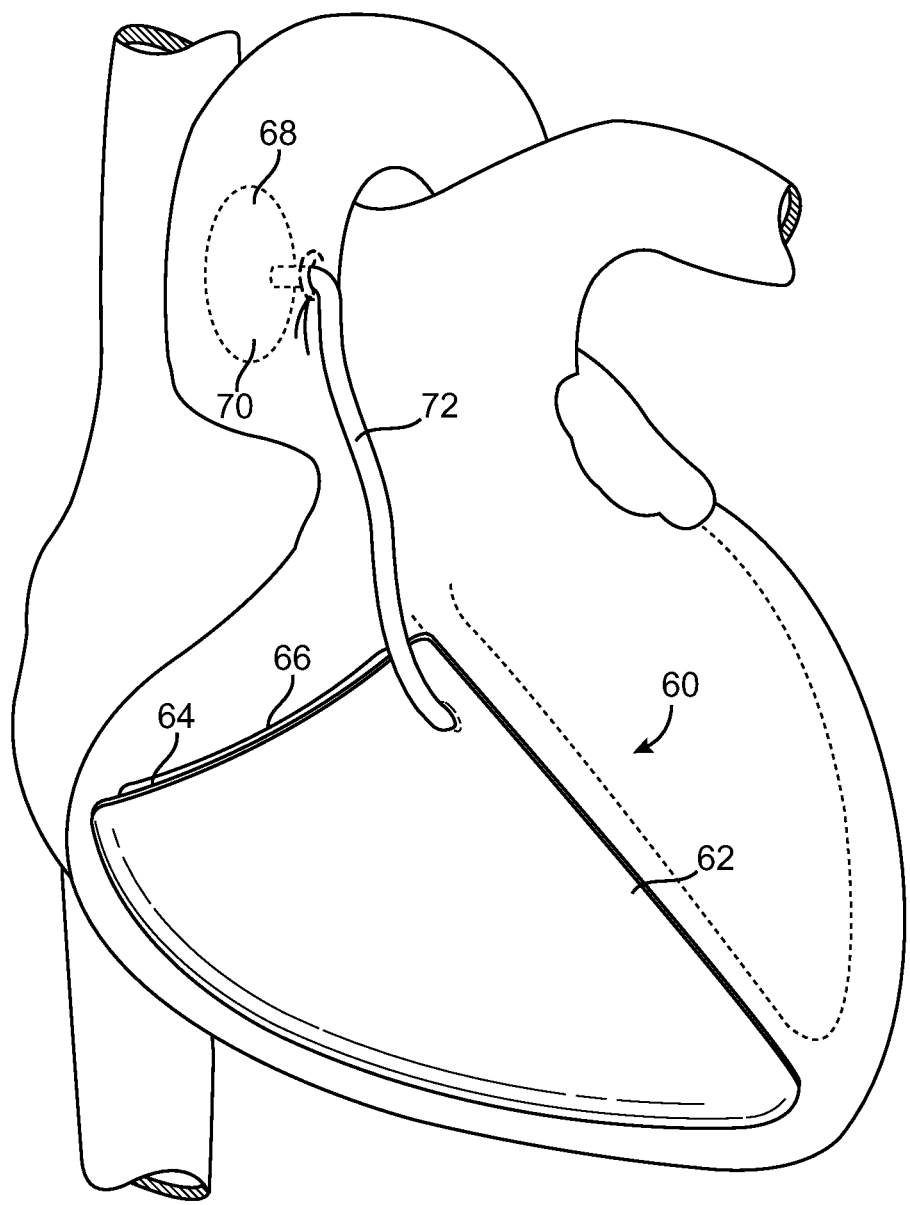
FIG. 8 shows yet another device for assisting the heart in pumping blood.
Figure 9:
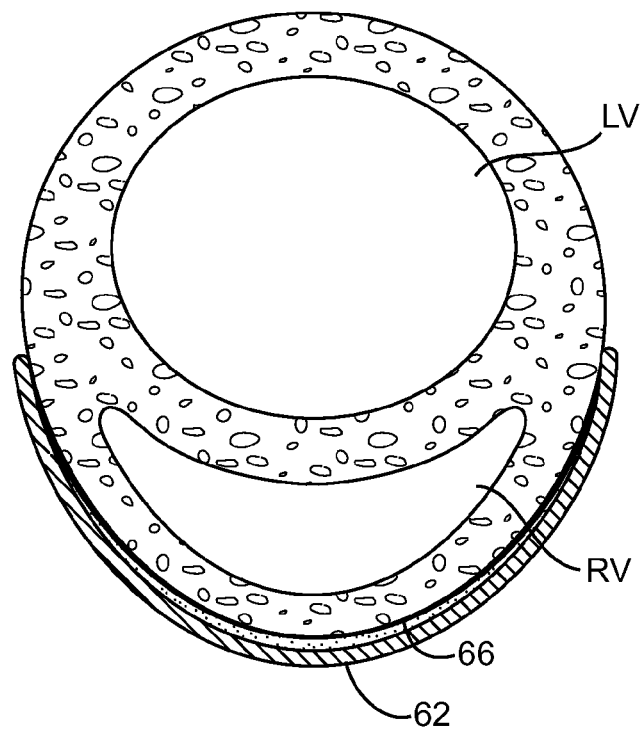
FIG. 9 shows a cross-sectional view of the heart with the bladder of FIGS. 5-8, 13 and 14 deflated.
Figure 10:
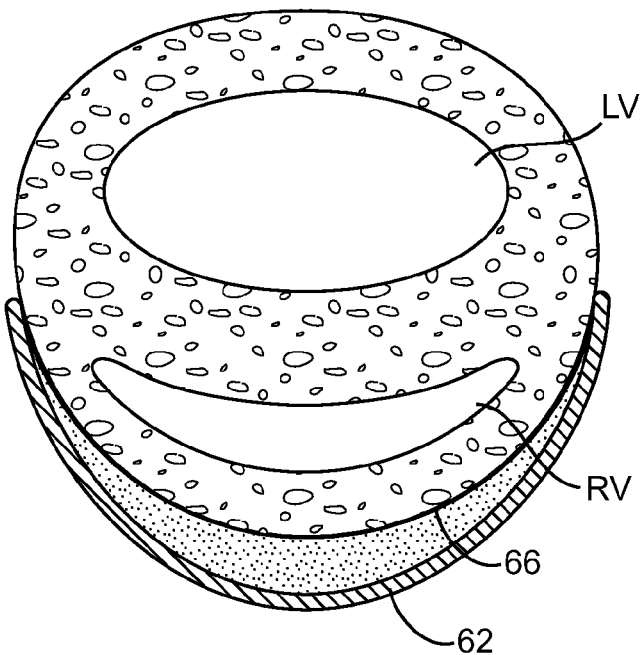
FIG. 10 shows the bladder of FIG. 9 inflated with a fluid when the right ventricular wall contracts.

Referring now to FIGS. 8-10, another device 60 for absorbing and delivering cardiac pumping energy is shown. The device 60 has an energy absorbing element 62 positioned adjacent an outer wall of the right ventricle which absorbs energy in the same manner as the energy absorbing element of FIGS. 5-7. The energy absorbing element 62 includes a bladder 64 positioned adjacent an exterior surface of the right ventricle. A flexible interior surface 66 of the bladder 64 may be attached to the epicardial surface of the right ventricular free wall so that the energy absorbing element 62 operates in essentially the same manner as the energy absorbing element 34 of FIGS. 5-7. When the right ventricle contracts, the bladder 64 expands and the pressure of the fluid inside the bladder 64 is reduced.

The device 60 also includes an energy delivery element 68 having an collapsible element 70 positioned inside the aorta or one or more of its branches. A tube 72 having a lumen extends from the collapsible element 70 through a vascular penetration in the wall of the aorta or other portion of the left heart such as the left atrium, left ventricle, or pulmonary veins. The collapsible element 70 is advanced into the aorta from its point of entry into the vascular system. This may entail advancing the collapsible element 70 through the mitral and aortic valves with the site of vascular puncture being sealed with a suitable closure such as a purse-string suture. The fluid in the collapsible element 70 is in pressure communication with fluid in the bladder 64 so that the collapsible element 70 is in an expanded state when the bladder 64 is compressed and in a collapsed state when the bladder 64 is expanded.

Figure 11:
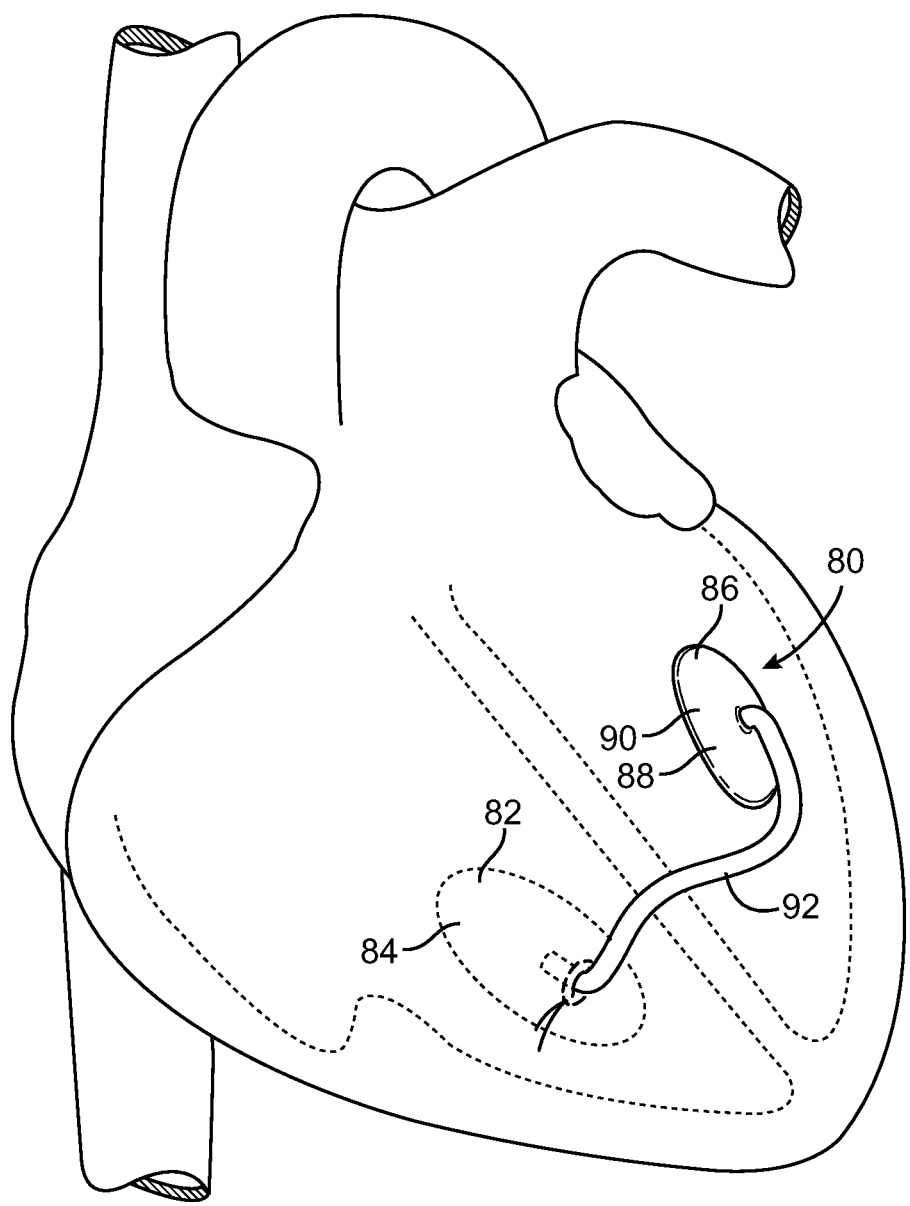
FIG. 11 shows still another device for assisting the heart in pumping blood.

Referring now to FIG. 11, still another device 80 for absorbing and delivering cardiac pumping energy is shown. The device 80 includes an energy absorbing element 82 having a compressible element 84 which is at least partially positioned within the right ventricle so that the element 82 is in fluid contact and in pressure communication with blood in the right ventricle. The compressible element 84 is configured to be compressed by the pressure of the blood inside the right ventricle during systole. The device 80 also includes an energy delivery element 86 having an expandable element 88 positioned adjacent an external surface of the left ventricle which exerts pressure on the external surface of the left ventricle to assist in pumping blood similar to other embodiments described herein. The expandable element 88 may be any suitable element such as a bladder 90. A tube 92 having a lumen extends between the energy absorbing element 82 and the energy delivery element 86 to provide pressure communication between the elements 82, 86. The tube 92 may penetrate any suitable part of the right heart or venous vasculature. For example, the tube 92 may penetrate the right atrium or vena cavae instead of the right ventricle and then pass through the tricuspid valve in order to position the bladder 90 inside the right ventricle.

Figure 12:
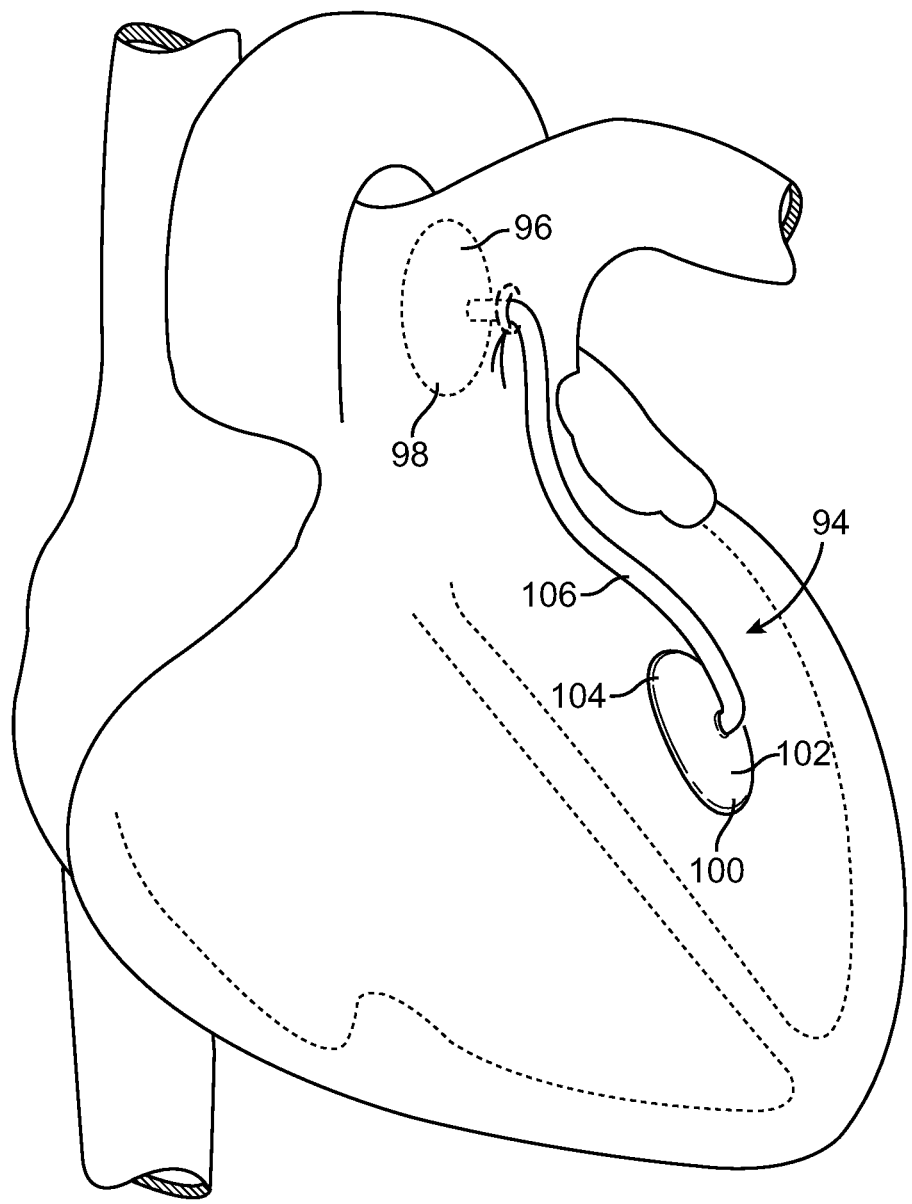
FIG. 12 shows another device for assisting the heart in pumping blood.

Referring now to FIG. 12, yet another device 94 for absorbing and delivering cardiac pumping energy is shown. The device 94 is similar to the device of FIG. 11 except that an energy absorbing element 96 has a compressible element 98 positioned in direct fluid communication with blood in the pulmonary artery or one or more of its branches. An energy delivery element 100 is similar to the energy delivery element 86 of FIG. 11 in that the element 100 has an expandable element 102, such as a bladder 104, positioned adjacent an external wall of the left ventricle. A tube 106 connects the expandable and compressible elements 98, 102 together to provide pressure communication between the elements 98, 102. The tube 106 may penetrate any part of the right heart or venous vasculature such as the wall of the pulmonary artery. A fluid tight seal may be obtained by using a purse string suture.

Figure 13:
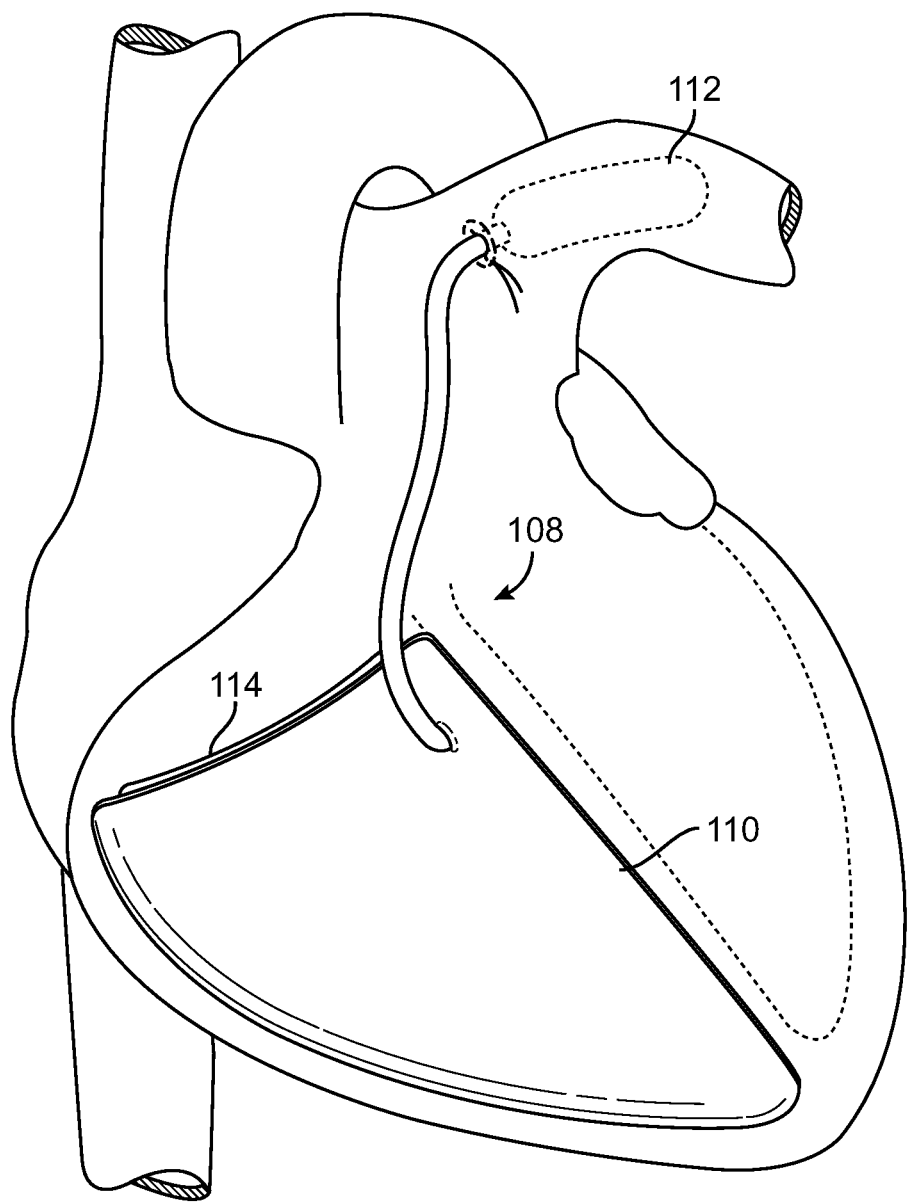
FIG. 13 shows another device for assisting the heart in pumping blood.

Referring to FIG. 13, another device 108 for absorbing and delivering cardiac pumping energy is shown. The device 108 has a first expandable and compressible element 110 and a second expandable and compressible element 112 which absorb and transfer energy between one another as they expand and contract. The first element 110 may be positioned adjacent the external wall of the right ventricle and may be formed in the same manner as the element 62 of FIG. 8 which is incorporated here. The second expandable and compressible element 112 is positioned within the pulmonary artery or one of its branches. The first element 110 has the bladder 114 which is expanded and compressed in the manner described above when the heart is beating. This configuration may reduce the stress on the right heart in patients with left ventricular dysfunction.

Figure 14:
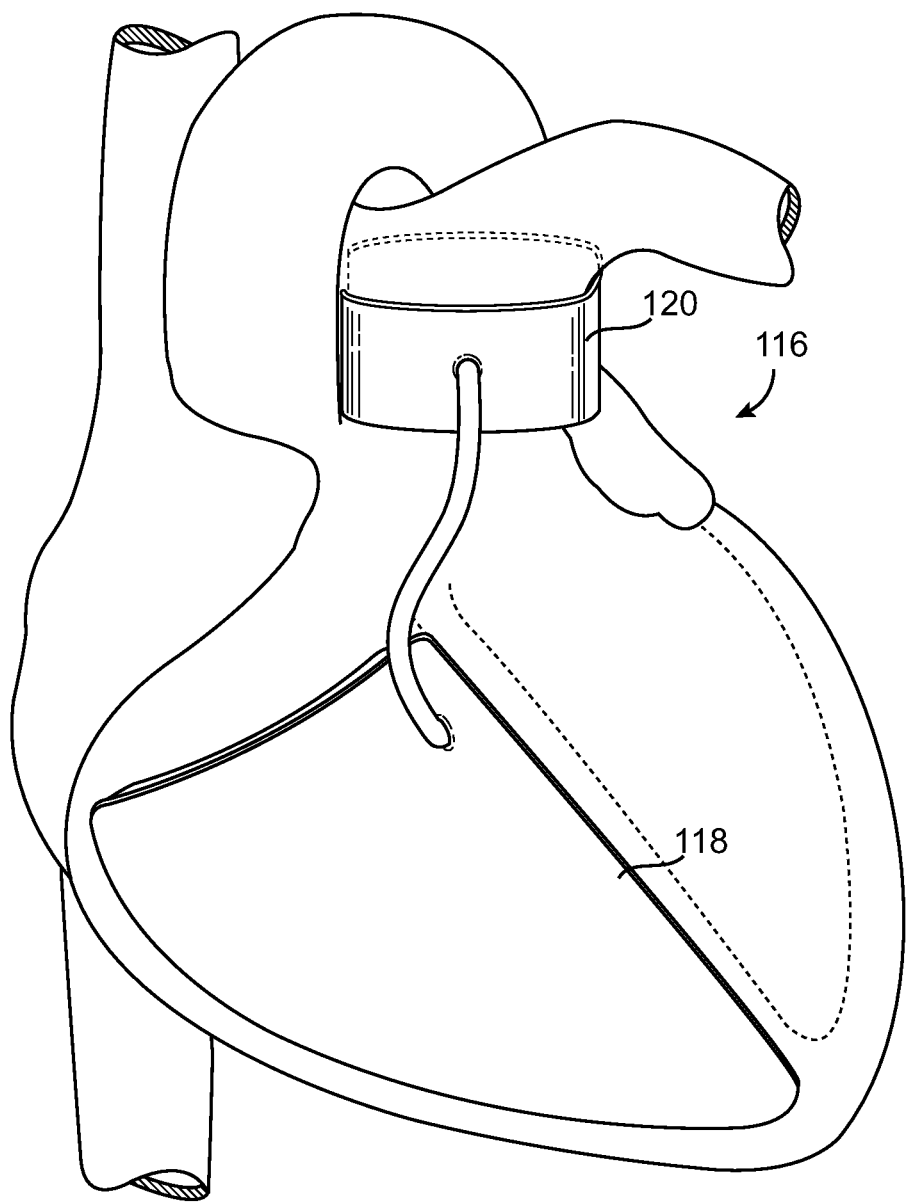
FIG. 14 shows yet another device for assisting the heart in pumping blood.

Referring now to FIG. 14, yet another device 116 for absorbing and delivering cardiac pumping energy is shown. The device 116 has a first expandable and compressible element 118 and a second expandable and compressible element 120 which absorb and transfer energy between one another as they expand and contract. The first element 118 may be positioned adjacent the external wall of the right ventricle and may be formed in the same manner as the corresponding structure of FIG. 8 which is incorporated here. The second expandable and compressible element 120 may be constructed similar to the energy absorbing element of FIG. 1 which is also incorporated here. This configuration may reduce the stress on the right heart in patients with left ventricular dysfunction.

Figure 15:
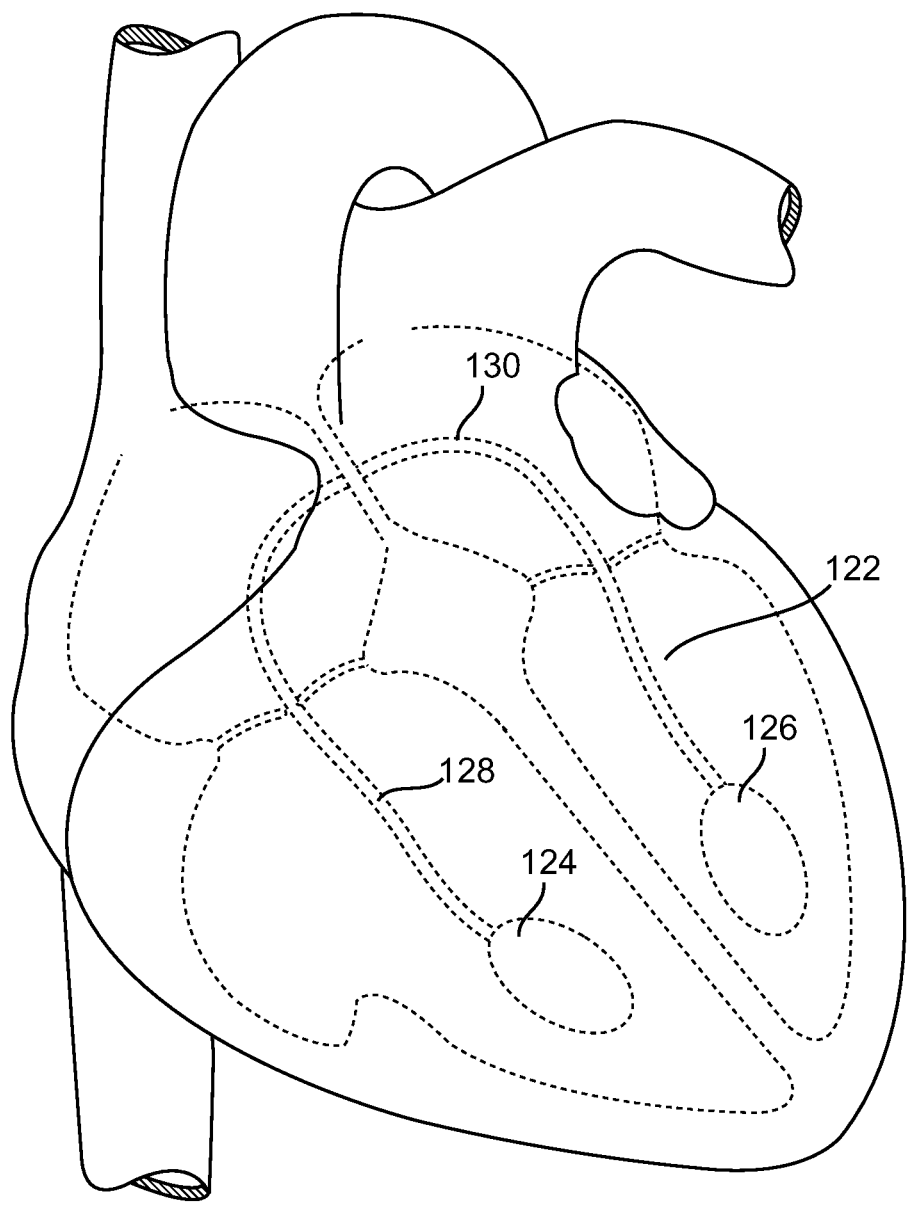
FIG. 15 shows another device for assisting the heart in pumping blood with an expandable and collapsible element positioned inside each of the ventricles.

Referring now to FIG. 15, still another device 122 for absorbing and delivering pumping energy is shown. The device 122 has a first expandable and collapsible element 124 in the right ventricle and a second expandable and collapsible element 126 in the left ventricle. The elements 124, 126 are filled with a fluid with the fluid in each element being in pressure communication with the other via a lumen 128 in a tube 130. The tube 130 may pass through both right and left ventricular walls and be sealed by purse string sutures or other suitable closure method. Alternatively the tube 130 may pass through other parts of the right and left vasculature and be routed into the respective ventricle along the blood path. The tube 130 may take an intravascular path which remains entirely inside the vascular system by passing through the interatrial septum and through the mitral and tricuspid valves as shown in FIG. 15. The device 122 may be suited for patients with right ventricular failure that have a relatively healthy left ventricle.

Figure 16:
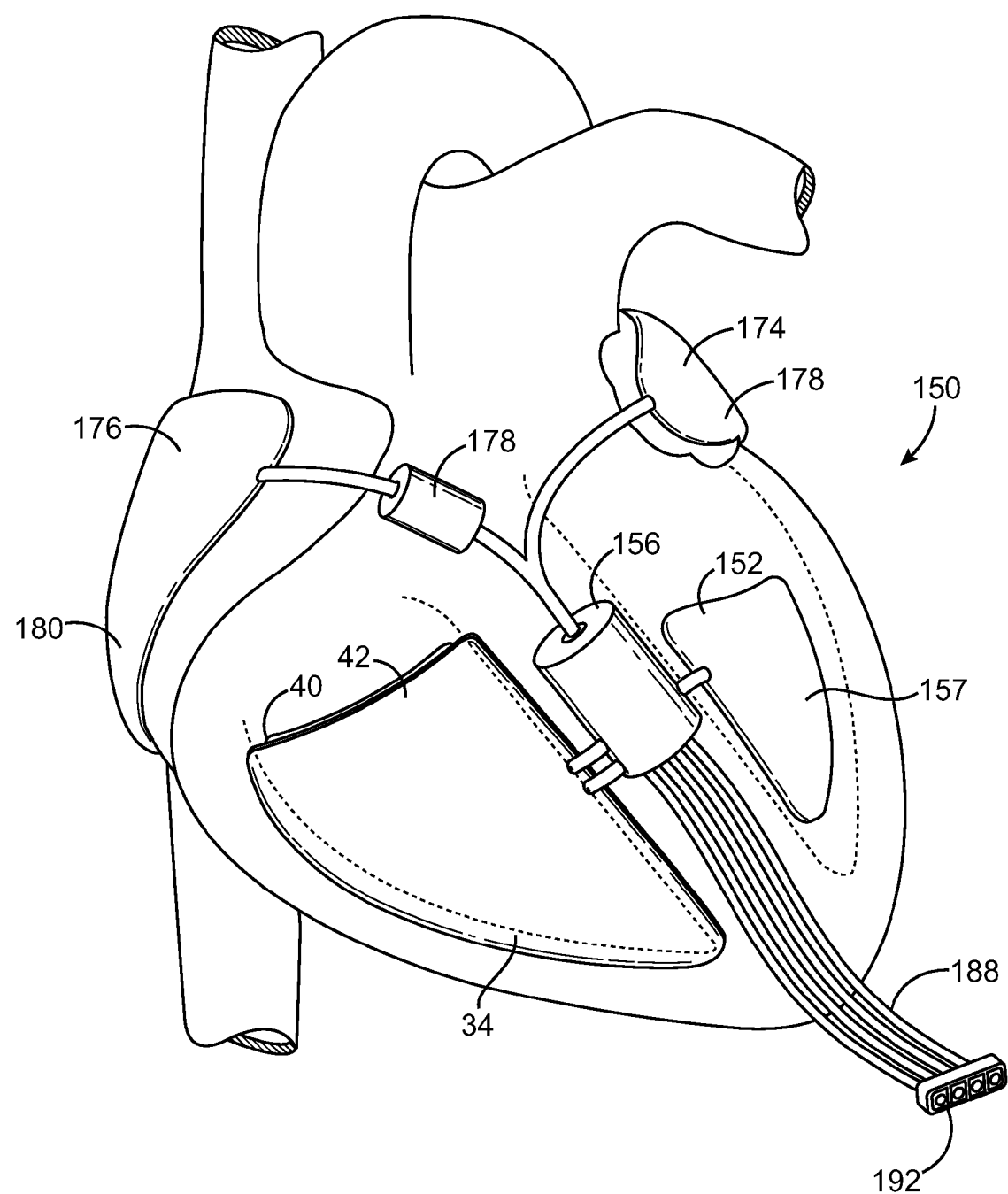
FIG. 16 shows another device for absorbing and delivering cardiac pumping energy.
Figure 17:
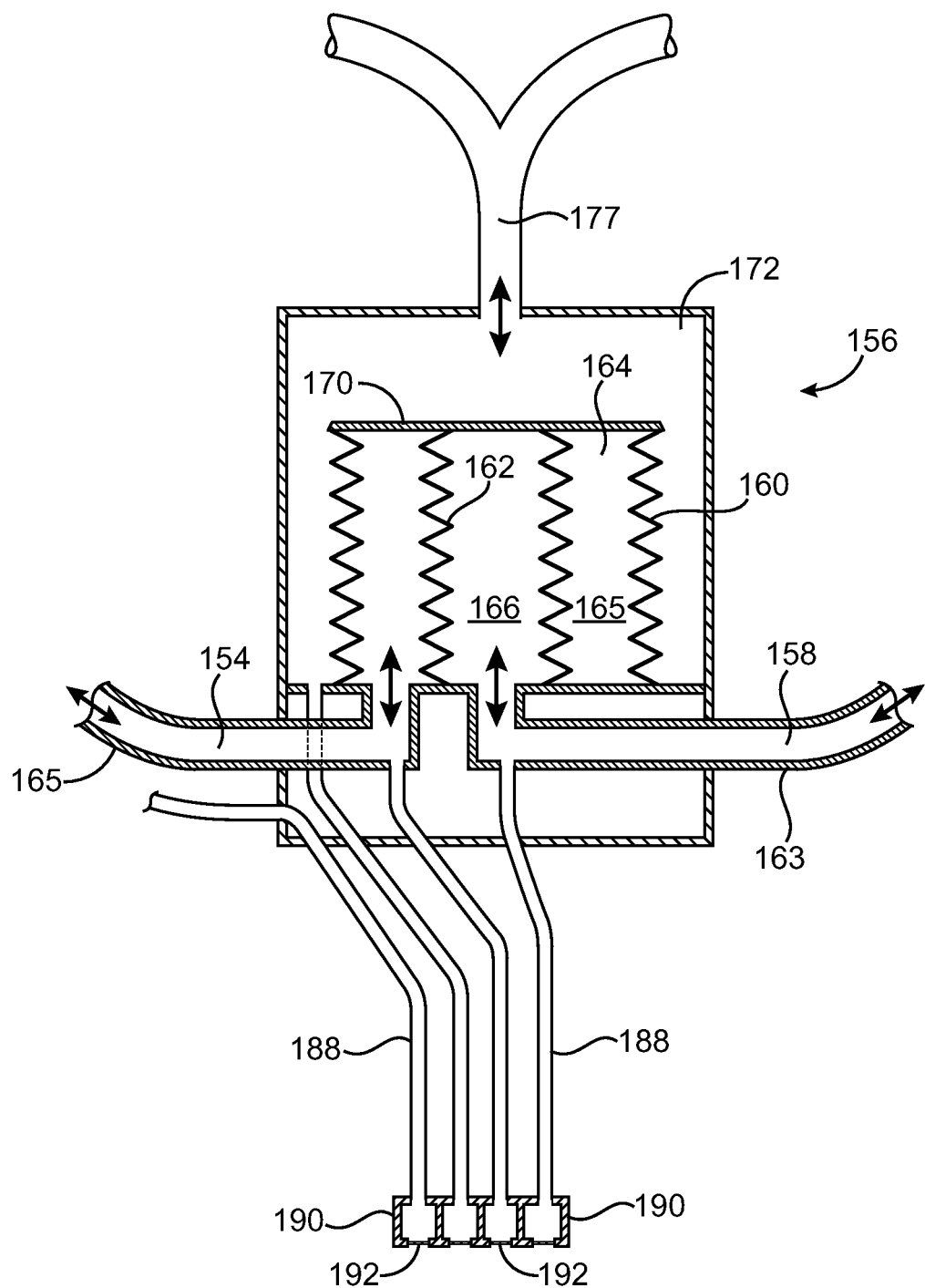
FIG. 17 shows a schematic cross-sectional view of a flow reversing element for the device of FIG. 16.
Figure 18:
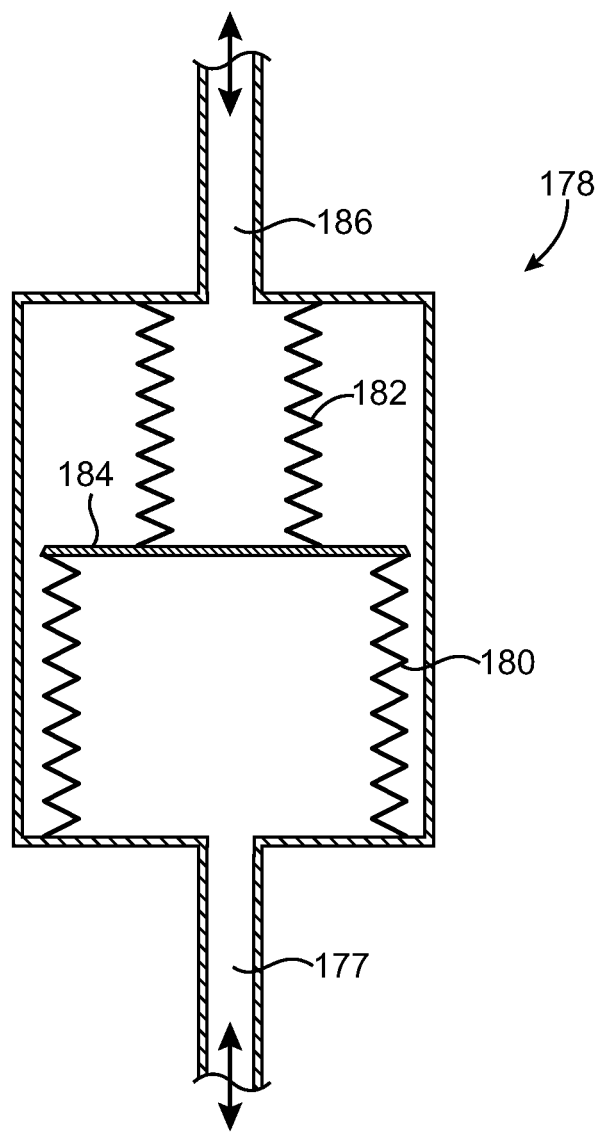
FIG. 18 shows a flow altering element for the device of FIG. 16.

Referring to FIGS. 16-18, still another device 150 for absorbing and delivering cardiac pumping energy is shown. The device 150 provides for epicardial contact on the left and right ventricles and may be practiced without penetrations in the heart or blood vessels and without direct contact with blood.

The device 150 includes the energy absorbing element 34 which is positioned against the exterior surface of the right ventricle and is described above with reference to FIGS. 5 7. All features and discussion of the element 34 are applicable and incorporated here. The energy absorbing element 34 absorbs pumping energy from the right ventricle and delivers the energy to an energy delivery element 152 positioned against the exterior surface of the left ventricle. The energy absorbing element 34 may have the bladder 40 attached to the rigid convex outer surface 42. The flexible interior surface 44 of the bladder 40 may be attached to the epicardial surface as described above (see FIG. 7).

The energy delivery element 152 is substantially the same as the energy delivery element 6 (see FIG. 1) with the difference being size and all features and discussion of the energy delivery element 6 are applicable to the energy delivery element 152 and incorporated here. The energy delivery element 152 provides pumping assistance to the left ventricle when an expandable element 157 is inflated to apply pressure to the exterior surface of the left ventricle.

A first fluid 154 moves between the energy absorbing element 34 and a flow reversing element 156 and a second fluid 158 moves between the flow reversing element 156 and the energy delivery element 152. The flow reversing element 156 helps to transmit pumping energy from the right ventricle to the left ventricle using the first and second fluids 154, 158. When the right ventricle contracts, the flexible interior surface 44 moves away from the rigid surface 42 thereby drawing the first fluid 154 into the energy absorbing element 34. As the first fluid 154 is drawn out of the flow reversing element 156, the second fluid 158 is forced out of the flow reversing element 156 and into the energy delivery element 152 which presses upon the exterior surface of the left ventricle thereby providing pumping assistance to the left ventricle. Conversely, when the first fluid 154 moves into the flow reversing element 156 from the energy absorbing element 34, the second fluid 158 also moves into the flow reversing element 156 from the energy delivery element 152. The flow reversing element 156 may accomplish the above described flow conditions in any suitable manner and is not limited to the specific embodiment now described.

Referring to FIG. 17, the flow reversing device 156 has a first tubular shaped bellows 160 and a second tubular shaped bellows 162. The first bellows 160 surrounds a first chamber 164 formed by an annular space 165 between the first and second bellows 160, 162. The second bellows 162 surrounds a second chamber 166. A movable wall 170 is coupled to both the first and second bellows 160, 162 so that the displacement of the ends of the bellows 160, 162 is essentially the same. Lumens 163, 165 couple the energy delivery element 152 and the energy absorbing element 34 to the flow reversing device 156.

The first and second bellows 160, 162 are positioned within a third chamber 172 which may be vented or may have a variable volume to accommodate the change in volume enclosed by the first and second bellows 160, 162. The change in volume of the third chamber 172 may also be accommodated by fluidly coupling the third chamber 172 to a left atrial element 174 and/or a right atrial element 176 which may provide pumping assistance to the atria. The atrial elements 174, 176 may each have an expandable element 178, 180 which may take the form of any of the energy absorbing or energy delivery elements described herein and the features of those elements are incorporated here. For example, the left and right atrial elements 174, 176 may be similar to the energy delivery element 6 (FIG. 1) and may have an expandable element 175 which exerts pressure on the exterior surface of the atrium. A third fluid 177 is passed between the left and right atrial elements 174, 176 and the third chamber 172 of the flow reversing element 156.

A flow altering element 178 may also be used to alter the flow rate and/or pressure of the third fluid 177 to be delivered to one or more of the atria. The flow altering element 178 has a first bellows 180 and a second bellows 182 with a common wall 184. The third fluid 177 fills the first bellows 180 and forces a smaller volume of a fourth fluid 186 to be delivered to the atrial element 176. In this manner, the flow rate and/or volume can be altered. Of course, any other flow element may be used to achieve the same result without departing from the scope of the invention.

The first, second and third fluids 154, 158 177 may be evacuated, replenished, mixed, tested, treated and/or changed through a number of leads 188 having ports 190. The ports 190 may have pierceable septums 192 or the like which are implanted just below the skin and may be accessed with conventional needles and the like.

A number of the embodiments described above are directed to devices which essentially assist the left ventricle in pumping blood. Of course, the right ventricle may also be assisted by the left ventricle in a similar manner without departing from the scope of the invention. In this case, the right heart structures would be replaced by the corresponding left heart structures and the left heart structures would be replaced by the corresponding right heart structures in all of the described embodiments. In other words, any references in the described embodiments to the vena cavae, right atrium, tricuspid valve, right ventricle, pulmonary valve, and pulmonary artery would be replaced with the pulmonary veins, left atrium, mitral valve, left ventricle, aortic valve, and aorta, respectively, and vice versa. This could be beneficial for heart failure patients whose left ventricle is healthier than the right.

In addition, the energy absorbed in accordance with the present invention may be used to help with any other blood pumping function such aventricular filling (i.e., diastole). This could be accomplished by applying the energy delivery elements described above for the aorta to the left atrium instead. By aiding with the contraction of the left atrium, left ventricular filling may be enhanced. In addition, by applying the energy delivery elements described above for the pulmonary artery to the right atrium instead, right ventricular filling may be enhanced. These approaches may be particularly useful for patients with diastolic disease.

The energy absorbed in accordance with the present invention may also be used to perform any other useful work other than pumping blood. To this end, the energy may also be converted to electrical energy to power any other device or store energy in an appropriate storage device such as a battery.

Although the present invention has been described in connection with the preferred embodiments described above it can be appreciated that many other devices and systems may be used which fall within the scope of the present invention. For example, the various embodiments and aspects of the devices described herein may be used alone or in any combination without departing from the scope of this invention.

What is claimed is:

1. A method for assisting the heart in pumping blood, comprising the steps of:
    providing a device for assisting the heart in pumping blood, the device having an energy absorbing element, an energy delivery element and a flow reversing element, the flow reversing element being coupled to the energy absorbing element to move a first fluid therebetween, the flow reversing element being coupled to the energy delivery element to move a second fluid therebetween;
    positioning the energy absorbing element to absorb pumping energy of at least one side of the heart from the group consisting of the right side of the heart and the left side of the heart, the absorbing element drawing the first fluid from the flow reversing element when absorbing pumping energy of the at least one side of the heart, the energy absorbing element being positioned against an exterior surface of the at least one side of the heart and being attached to the exterior surface of the at least one side of the heart;
    forcing the second fluid from the flow reversing element, the flow reversing element using energy absorbed from the at least one side of the heart to force the second fluid out of the flow reversing element; and
    delivering the second fluid to the energy delivery element which has been forced out of the flow reversing element during the forcing step to provide pumping assistance to an other side of the heart, the energy delivery element applying pressure to an exterior surface of the other side of the heart.

2. The method of claim 1, wherein:
    the providing step is carried out with the energy delivery element including an expandable element.

3. The method of claim 1, wherein:
    the positioning step is carried out with the energy absorbing element being positioned to absorb energy of the right ventricle.

4. The method of claim 1, wherein:
    the delivering step is carried out with the other side of the heart being the left ventricle.

5. The method of claim 1, wherein:
    the providing step is carried out with the energy absorbing element having an expandable element, the first fluid moving into and out of the expandable element as the expandable element expands and contracts, the energy delivery element also having an expandable element, the second fluid moving into and out of the expandable element as the expandable element expands and contracts.

6. The method of claim 1, wherein
    the providing step is carried out with a flow altering element positioned between the energy delivery element and the flow reversing element, the flow altering element receiving the second fluid at a flow rate and delivering a third fluid at an altered flow rate to the energy delivery element.

7. The method of claim 1, wherein:
    the providing, positioning, receiving and delivering steps are carried out without the need for penetrations in the heart and without direct contact with blood.

8. A device for assisting the heart in pumping blood, comprising:
    a flow reversing element;
    an energy absorbing element coupled to the flow reversing element, the energy absorbing element transferring a first fluid to and from the flow reversing element; and
    an energy delivery element coupled to the flow reversing element, the energy delivery element transferring a second fluid to and from the flow reversing element, the energy delivery element expanding as the second fluid moves into the second delivery element;
    the flow reversing element receiving the first fluid and moving the second fluid out of the fluid reversing element toward the energy delivery element in response to the first fluid entering the flow reversing element.

9. The device of claim 8, wherein:
    the energy delivery element includes an expandable element, the expandable element exerting external pressure to a vascular structure to assist in pumping blood.

10. The device of claim 8, wherein:
    the expandable element of the energy delivery element applies pressure to the exterior surface of a ventricle; and
    the energy absorbing element and the energy delivery element are implantable without the need for penetrations in the heart or blood vessels and without direct contact with blood.

11. The device of claim 8, wherein:
    the energy absorbing element absorbs pumping energy from the heart from the right ventricle, the energy absorbing elemnet having an expandable element attached to an exterior surface of the right ventricle.

12. The device of claim 8 wherein:
    the energy absorbing element has an expandable element, the first fluid moving into and out of the compressible element as the expandable element expands and contracts; and
    the energy delivery element also having an expandable element, the second fluid moving into and out of the expandable element as the expandable element expands and contracts.

13. The device of claim 8, further comprising:
    a flow altering element positioned between the energy delivery element and the flow reversing element, the flow altering element receiving the second fluid at a flow rate and altering the flow rate by delivering a third fluid at an altered flow rate to the energy delivery element.

14. The device of claim 8, wherein:
    the energy delivery element is configured to be positioned against an exterior surface of an atrium for delivery of pumping energy to the atrium.

15. The device of claim 8, wherein:
the energy delivery element is configured to be positioned on a side of the heart consisting of the right side of the heart and the left side of the heart; and
the energy absorbing element is configured to be positioned on a side of the heart opposite the energy delivery element.

* * * * *